United States Patent [19]

Bognar et al.

[11] 4,144,236
[45] Mar. 13, 1979

[54] 6-DEOXY-6-AZIDO-14-HYDROXY-7,8-DIHYDROISOMORPHINE OR A PHARMACEUTICALLY ACCEPTABLE SALT THEREOF

[75] Inventors: Reszö Bognar; Sándor Makleit; Géza Kiss; Sándor Berényi; Teréz Mile, all of Debrecen; Jozsef Knoll, Budapest; Sándor Elek, Tiszavasvari; István Gyokér, Tiszavasvari; Attila Zoltai, Tiszavasvari; György Tóth, Tiszavasvari; Laszlo Litkei, Tiszavasvari, all of Hungary

[73] Assignee: Alkaloida Vegyeszeti Gyar Tiszavasvari, Tiszavasvari, Hungary

[21] Appl. No.: 795,443

[22] Filed: May 10, 1977

Related U.S. Application Data

[63] Continuation-in-part of Ser. No. 702,586, Jul. 6, 1976, abandoned, which is a continuation of Ser. No. 502,729, Sep. 3, 1974, abandoned, which is a continuation-in-part of Ser. No. 681,214, Apr. 28, 1976, abandoned.

[30] Foreign Application Priority Data

Sep. 4, 1973 [HU] Hungary ............................. AA 750

[51] Int. Cl.$^2$ .................. C07D 489/06; A61K 31/485
[52] U.S. Cl. ........................................ 546/46; 424/260
[58] Field of Search .......................... 260/285; 702/586

[56] References Cited

U.S. PATENT DOCUMENTS

| | | | |
|---|---|---|---|
| 3,880,862 | 4/1975 | Meltzer | 260/285 |
| 3,880,863 | 4/1975 | Meltzer | 260/285 |
| 3,882,127 | 5/1975 | Meltzer | 260/285 |

OTHER PUBLICATIONS

Knoll et al. (W), Archives Internationales de Pharmacodynamie et de Therapie, vol. 210, No. 2, Aug. 1974, pp. 241-249.
Bognar et al., Acta Chim (Budapest), 58 (2), pp. 203-205 (1968).
Bognar et al., Magy. Kem. Foly., 74 (11), pp. 526-530 (1968).
Knoll et al., Orvostudomany, 22 (3-4), pp. 265-284 (1971).
Bognar et al., Magy. Kem. Foly., 78 (5), pp. 223-228 (1972).
Bognar et al., Acta Chim (Budapest), 74 (1), pp. 99-109 (1972).

*Primary Examiner*—Donald G. Daus
*Assistant Examiner*—Diana G. Rivers
*Attorney, Agent, or Firm*—Karl F. Ross

[57] ABSTRACT

A process for the preparation of pharmaceutically acceptable 3-protected derivatives of 6-deoxy-6-azido-14-hydroxy-7, 8-dihydroisomorphine, selected from the group which consists of 3-O-acetyl-6-deoxy-6-azido-14-hydroxy-7, 8-dihydroisomorphine, 3-O-tetrahydropyranyl-6-deoxy-6-azido-14-hydroxy-7, 8-dihydroisomorphine and 3-O-methylenemethoxy-6-deoxy-6-azido-14-hydroxy-7, 8-dihydroisomorphine, and the salts of these compounds which comprise the following steps:

blockin the hydroxy in position 3 of 14-hydroxy-7, 8-dihydromorphine with a moiety selected from the group which consists of acetyl, tetrahydropyranyl, and methylenemethoxy; and azidiylating position 6 of the compounds formed in a step (a) thereby removing the hydroxy formerly in that position.

1 Claim, No Drawings

6-DEOXY-6-AZIDO-14-HYDROXY-7,8-DIHYDROISOMORPHINE OR A PHARMACEUTICALLY ACCEPTABLE SALT THEREOF

CROSS-REFERENCE TO RELATED APPLICATIONS

This application is a continuation-in-part of Ser. No. 702,586 filed July 6, 1976 now abandoned as a continuation of Ser. No. 502,729 filed Sept. 3, 1974 (now abandoned) and is related to Ser. No. 681,214 filed Apr. 28, 1976 now abandoned as a continuation-in-part of the latter.

This invention relates to new 7,8-dihydroisomorphine derivatives and to a process for the preparation thereof. More particularly, this invention relates to the new compounds, 6-deoxy-6-azido-7, 8-dihydroisomorphine derivatives and 6-deoxy-6-azido-14-hydroxy-7, 8-dihydroisomorphine as well as to its 3-protected derivatives, or the salts of these compounds. These compounds can be prepared according to the invention as follows: The hydroxy groups attached to positions 3 and 6 of 7, 8-dihydromorphine and of 14-hydroxy-7, 8-dihydromorphine are blocked by appropriate protecting groups, the obtained compound is reacted with a metal azide or a compound furnishing azido groups under the reaction conditions and, if desired, the O-blocking group attached to position 3 of the obtained intermediate is split off, and/or, if desired, the product is converted into its salt, or the free base is liberated from the salt.

The new compounds according to the invention can be used in human therapy as analgesic agents and are especially effective as antitussive compounds. They can be administered either alone or together with other morphine derivatives or other biologically active substances. Some representatives of the new compounds according to the invention can be used as intermediates in the synthesis of morphine derivatives. Thus they promote the development of morphine chemistry.

7, 8-Dihydromorphine and 14-hydroxy-7,8-dihydromorphine, used as starting in the process accarding to the invention, are known compounds. The hydroxy groups attached to positions 3 and 6 of the molecules can be protected, prior to azidolysis, by several methods. The hydroxy group in position 3 is protected preferably with an acyl, tetrahydropyranyl or methylenemethoxy group; these groups can be removed either during or after azidolysis.

If 3-substituted derivatives are to be prepared, the hydroxy group attached to position 3 of 7, 8-dihydromorphine and of 14-hydroxy-7,8-dihydromorphine is protected with an acyl, alkyl, aralkyl or aryl group, and the protecting group is not removed during or after azidolysis, either.

According to a preferred method of the invention the hydroxy group attached to position 3 is protected by subjecting the dihydroxy compounds to partial acylation, particularly acetylation, formylation or benzoylation. As esterifying agents, preferably the corresponding anhydrides are used, but other esterifying agents can be applied as well.

The hydroxy group attached to position 6 can also be blocked with an acyl group. If more severe acylating conditions are used, the acylation of the hydroxy groups attached to position 3 and 6 takes place simultaneously, and 3, 6-diacyl derivatives are formed.

Particularly preferred intermediates for the azidolysis step can be formed by esterifying the hydroxy group in position 6 with an arylsulfonyl or alkylsulfonyl group, among which tosyl, mesyl, brosyl, nosyl and mesityl groups are the most preferred.

If, for example, the hydroxy group in position 3 is blocked by partial esterification using acetic anhydride, and subsequently the hydroxy group in position 6 is esterified with p-toluenesulfonyl chloride, to yield an intermediate, the azidolysis of which proceeds with excellent yield, is obtained.

Azidolysis is an important step of the synthesis according to the invention. In this step the substituted hydroxy group in position 6 is replaced by an azido group; this reaction is carried out by contacting the blocked compound with a substance furnishing azido groups. As reagents, metal azides, e.g., sodium or potassium or lithium azide, or substances furnishing azido groups during their decomposition can be used.

The relatively unstable blocking groups attached to position 3 split off easily under the conditions of azidolysis; thus the hydroxy group in position 3 can be deblocked simultaneously with the introduction of the azido group. In this way e.g., a 3-O-acetyl derivative can be converted easily into the corresponding 3-hydroxy compound.

The compounds prepared as described above can be isolated from the reaction mixture either as free bases or in the form of their salts.

The salts obtained in the above reaction can be converted into other salts having greater pharmacological value or more favorable physicochemical properties. Of the salts the tartarates, acetates, salicylates, benzoates, hydrochlorides and formates are to be mentioned.

The new compounds according to the invention can be converted into pharmaceutical compositions suitable for oral, parenteral or rectal administration. The pharmaceutical compositions can be prepared by known techniques, using conventional carriers and/or auxiliary agents.

Of the compounds according to the invention 6-deoxy-6-azido-14-hydroxy-7, 8-dihydroisomorphine possesses outstanding therapeutic properties. When comparing this compound with the most important narcotics and analgesics we have found that 6-deoxy-6-azido-14-hydroxy-7, 8-dihydroisomorphine has more favorable therapeutical indices than any of the known substances with similar biological activities, also including 6-deoxy-6-azido-7, 8-dihydroisomorphine proposed earlier for the same purpose (Acta Chim. Acad. Sci. Hung. 58, 203: 1968, Orvostudomany 22, 265: 1971). A further advantage of the new compounds is that addiction occurs less frequently than with other analgesics, which where morphine derivatives are concerned, is an essential factor in judging therapeutic value.

The invention is represented by the following non-limiting examples.

EXAMPLE 1

10 g. of 14-hydroxy-7, 8-dihydromorphine are suspended in 1 l. of water, and 100 g. of sodium carbonate are added to the suspension. 50 ml. of acetic anhydride are added, in three equal portions, to the vigorously stirred mixture. When the bubbling ceases, the mixture is stirred for a while, and then extracted with 5×200 ml. of chloroform. The chloroform solutions are combined, washed with 2×50 ml. of sodium hydroxide and 200 ml. of water, dried over magnesium sulfate, and evaporated to dryness. 3-O-Acetyl-14-hydroxy-7, 8-dihydromorphine is obtained with almost quantitative yield. The obtained product can be further processed without any purification step.

EXAMPLE 2

10 g. of 3-O-acetyl-14-hydroxy-7, 8-dihydromorphine are dissolved in 40 ml. of dry pyridine, and a solution of 7 g. of p-toluenesulfonyl chloride in 40 ml. of dry pyridine is added dropwise to the stirred solution at a temperature between 0° and 5° C. The reaction mixture is stirred for a while, then allowed to stand at room temperature overnight the mixture is poured into 1 l. of saturated aqueous sodium bicarbonate solution, and extracted with 3×200 ml. of chloroform. The chloroform solutions are combined, washed with 2×100 ml. of water, dried over magnesium sulfate, and evaporated to dryness. The residue is triturated with dry ether to yield crystalline 3-O-acetyl-6-O-tosyl-14-hydroxy-7, 8-dihydromorphine; m.p.: 193°–194° C.

EXAMPLE 3

10 g. of 3-O-acetyl-6-o-tosyl-14-hydroxy-7, 8-dihydromorphine are dissolved in 310 ml. of dimethylformamide, and a solution of 20 g. of sodium azide in 46 ml. of water is added. The reaction mixture is heated at 100° C. for 24 hours, thereafter poured into 1 l. of water, and extracted with 3×250 ml. of chloroform. The chloroform solutions are combined, washed with 2×100 ml. of saturated aqueous sodium chloride solution, dried over magnesium sulfate, and evaporated to dryness at a temperature not exceeding 60° C. The residue is triturated with acetone to obtain crystalline 6-deoxy-6-azido-14-hydroxy-7, 8-dihydroisomorphine with an excellent yield. The product melts at 222°–223° C.

EXAMPLE 4

One proceeds as described in Example 2, with the difference that methanesulfonyl chloride is used as the esterifying agent. Crystalline 3-O-acetyl-6-O-mesyl-14-hydroxy-7, 8-dihydromorphine, melting at 179°–181° C., is obtained.

EXAMPLE 5

10 g. of the 6-O-tosyl or 6-O-mesyl derivative, prepared as described in Examples 2 or 4, are dissolved in 300 ml. of N-methyl-pyrrolidone and subjected to azidolysis as described in Example 3. 6-Deoxy-6-azido-14-hydroxy-7, 8-dihydroisomorphine, melting at 222°–223° C., is obtained with a good yield. The reaction can be carried out in hexamethylphosphorous triamide as well.

EXAMPLE 6

1.5 g. of 6-deoxy-6-azido-7, 8-dihydroisomorphine and 15 g. of sodium bicarbonate are suspended or dissolved, respectively, in 150 ml. of water with stirring. 7.5 ml. of acetic anhydride are added, in three portions, to the stirred mixture, the next portion being added only when the bubbling of the mixture ceases. After the addition the mixture is stirred for 5 minutes; thus the reaction takes about 35 to 40 minutes. The aqueous solution is extracted with 3×15 ml. of chloroform. The chloroform solutions are combined, washed with 2×10 ml. of water, dried over magnesium sulfate, filtered and the filtrate is evaporated to dryness. The obtained 1.6 g. of resinous substance are dissolved in 21.5 ml. of warm absolute ethanol, and a hot solution of 0.67 g. of D-tartaric acid in 7.5 ml. of ethanol is added. The crystals separating upon cooling are filtered off, to yield 3-O-acetyl-6-deoxy-6-azido-7, 8-dihydroisomorphine bitartrate. The product melts at 178°–180° C. $(a)_D = -117°$ (c = 0.45, in water).

EXAMPLE 7

14.85 g. of 3-O-ethyl-7, 8-dihydromorphine are dissolved in 60 ml. of absolute pyridine, and a solution of 6.014 g. (4.06 ml.) of methanesulfonyl chloride in 60 ml. of absolute pyridine are added dropwise to the stirred solution within about 20 minutes. During the addition the temperature of the mixture is kept between 0° and 5° C. The mixture is stirred for an additional 2 hours, thereafter it is allowed to stand at room temperature overnight. The reaction mixture is poured into 1.5 l. of saturated aqueous sodium bicarbonate solution, and processed as described in the preceding Examples. The solvents, including pyridine, are removed by distillation, and the obtained resinous substance is dissolved in warm absolute ether. The substance starts soon to crystallize. This way 11.86 g. (64%) of 6-O-mesyl-dihydro-dionine are obtained; m.p.: 135°–136° C., $(a)_D = -96.1°$ (c = 0.52, in chloroform).

EXAMPLE 8

11.0 g. of 6-O-mesyl-dihydro-dionine are dissolved in 330 ml. of dimethylformamide, and a solution of 18.19 g. of sodium azide in 51.2 ml. of water is added. The homogeneous reaction mixture is warmed at 100° C. for 24 hours, thereafter cooled and poured onto 1.65 l. of water. The aqueous solution is extracted with 4×200 ml. of chloroform. The chloroform solutions are combined, washed with 2×110 ml. of saturated aqueous sodium chloride solution, dried over magnesium sulfate, filtered, and the filtrate is evaporated at a temperature not exceeding 50° C. The obtained resinous product is dissolved in absolute ether. The separated fluffy substance is filtered off, and the filtrate is evaporated to dryness. 6.8 g. of a pure, resinous substance are obtained. This substance is dissolved in 102 ml. of dry ethanol, and a hot solution of 3 g. of D-tartaric acid in 30 ml. of ethanol is added. The tartrate separates as yellow crystal plates. The product is recrystallized twice from water. This way 3-O-ethyl-6-deoxy-6-azido-7, 8-dihydroisomorphine bitartrate, melting at 55°–56° C., is obtained. $(a)_D = -192°$ (c = 0.5, in chloroform).

The bitartrate is dissolved in water, and the solution is rendered alkaline with sodium carbonate, to yield crystalline 3-O-ethyl-6-deoxy-6-azido-7, 8-dihydroisomorphine.

The data referring to the biological activities of 6-deoxy-6-azido-14-hydroxy-7, 8-dihydroisomorphine (hereinafter Compound "A") are summarized in the following Tables.

Tables 1 to 3 indicate the data referring to the analgesic activity of Compound "A." For comparison purposes the respective data of 5 known analgesics are also given. The 95% confidence limits are indicated in brackets.

In Table 4 the results of the physical dependency disposition test (spring-test) carried out for 2 days on mice are given. The results obtained for Compound "A" are compared with those obtained for morphine and azidomorphine, respectively.

Table 1

| Compound | $LD_{50}$ mg./kg.s.c. (rats) | $ED_{50}$(hot plate[+]) mg./kg.s.c. (rats) |
|---|---|---|
| Morphine | 310 (267.2–349.6) | 4.7 (2.9–7.8) |
| Methadone | 28 (24.5–31.9) | 1.9 (1.4–2.5) |
| Petidine | 280 (194.4–403.2) | 4.9 (4.1–5.5) |
| Pentazocine | 280 (241.3–328.8) | 9.1 (4.78–17.29) |
| Azidomorphine | 13 (11.7–19.0) | 0.016 (0.0067–0.038) |
| Compound "A" | 200 (161.2–248.6) | 0.012 (0.0071–0.020) |

[+] Woolfe,G. and McDonald,A.P.: J.Pharmace. Exp.Ther. 80,300 (1944)

Table 2

| Compound | Therapeutical index $LD_{50}/ED_{50}$ (rats) | $ED_{50}$ (tail flick test[++]) s.c. mg./kg. (rats) |
|---|---|---|
| Morphine | 66 | 1.8 (1.08–3.15) |
| Methadone | 14.7 | 1.6 (1.1–2.3) |
| Petidine | 57.1 | 4.3 (2.7–6.6) |
| Pentazocine | 30.8 | 12 (8.1–18.3) |
| Azidomorphine | 812.5 | 0.012 (0.0089–0.016) |
| Compound "A" | 16666.6 | 0.029 (0.022–0.037) |

[++] D'Amour,D.E. and Smith,D.L.: J.Pharm.Expt.Ther. 72. 74.(1941)

Table 3

| Compound | Therapeutical index $LD_{50}/ED_{50}$ (rats) | $ED_{50}$(Writhing test[+++])s.c. mg./kg. (mice) | Longitudinal muscle preparate (guinea pig[++++]) $LD_{50}$ mg./kg. |
|---|---|---|---|
| Morphine | 172,2 | 0,69 (0.65–0.76) | 46.0 |
| Methadone | 17.5 | 0.71 (0.48–1.05) | — |
| Petidine | 65.1 | 3.3 (1.49–6.93) | — |
| Pentazocine | 23.0 | 8.1 (5.46–12.3) | — |
| Azidomorphine | 1083.3 | 0.013 (0.009–0.018) | 0.63 |
| Compound "A" | 6896.5 | 0.051 (0.036–0.070) | 0.7 |

[+++] Van der Wende,C. and Margolin,S.: Fed.Proc. 15, 494 (1956)
[++++] Paton,W.D.M. and Vizi,E.S.:Br.J.Pharmac. 35, 10 (1969)

Table 4

| Compound | Total dosage* | Total dosage $ED_{50}$ (analgesic)[++] | Haloxone 100mg./kg. Average jump per mouse | Change on the 2nd day Jumping mice/examined mice |
|---|---|---|---|---|
| Morphine | 100 | 20 | 9.7 | 20/25 |
| | 200 | 40 | 46.4 | 25/25 |
| | 400 | 80 | 42.7 | 25/25 |
| | 1000 | 200 | 48.7 | 25/25 |
| Azidomorphine | 1 | 40 | 0.0 | 0/25 |
| | 10 | 400 | 1.4 | 10/25 |
| | 40 | 1600 | 10.1 | 19/25 |
| | 70 | 2800 | 7.4 | 12/25 |
| Compound "A" | 10 | 800 | 0.9 | 3/25 |
| | 70 | 5600 | 3.8 | 14.25 |

[+]The total dosage was added in(rape)ritoneally in seven, gradually increasing increments, within 26 hours.
[++]$ED_{50}$ (analgesic): morphine: 5 mg./kg. i.p., azidomorphine: 0.025 mg./kg. i.p., Compound "A": 0.0125 mg./kg. i.p. (measured by the hot plate test)

METHODS: Anti-Tussive Activity

The anti-tussive activity in rats was tested by the method of Gosswald. Wistar rats weighing 130 to 180 g were placed in a plexi box (23 × 22 × 11 cm) and cough responses were elicited by citric acid aerosol (10%). The latency period of cough was measured before and after drug administration. The control latency was determined 18 hours before the drug administration. Animals with less than 60 second control latency were used for the experiments. The average control latency was found to be 29.41 ± 9.61 seconds. Each animal was exposed to citric acid aerosol for a period of 3 minutes 30 seconds and 60 minutes after drug administration. The dose of a drug which inhibited coughing over 90 seconds was considered effective. Ten animals were used at each dose level. The anti-tussive dose ($AtD_{50}$) was calculated according to Litchfield and Wilcoxon. The drugs were administered by subcutaneous and oral routes.

Anti-tussive activity in cats was determined by the method of Domenjoz. Cats weighing 2.5 to 3.5 kg were anesthetized with an i.p. dose of 30 mg per kg of sodium pentobarbitone. The superior laryngeal nerve was exposed and cough was induced by electrical stimulation of the nerve (1 msec., 10 Hz, 5 to 10 V for 10 seconds) through bipolar platinum electrodes every 5 minutes. The cough responses were measured by means of a Marey-tambour connected to a face mask and recorded on a smoked paper. Drugs were given intravenously in increasing doses. The effect of each dose was measured on at least five cats. The effects of the drug was calculated from the changes of amplitude of cough curves. If no coughing was produced by two successive stimulations, the dose was taken as the effective anti-tussive dose ($AtD_{100}$). The anti-tussive dose ($AtD_{50}$) which reduces the control response by 50% was calculated by the method of Litchfield and Wilcoxon.

Tables 5 and 6 show the inhibitory activity of 14-hydroxy-6-azidomorphine and reference anti-tussive on citric acid aerosol induced cough in rats.

Table 5

| Compound | $AtD_{50}$mg/kg s.c. | Ratio codeine/drug |
|---|---|---|
| Codeine | 19.0 (15.08–23.94) | 1.00 |
| Azidocodeine | 1.57 (1.20–2.41) | 12.10 |
| 14-OH-azidocodeine | 0.82 (0.71–0.95) | 23.17 |
| Morphine | 3.00 (1.84–4.25) | 6.33 |
| Azidomorphine | 0.034 (0.023–0.049) | 558.82 |
| 14-OH-azidomophine* | 0.021 (0.013–0.035) | 904.76 |

*6-deoxy-6-azido-14-hydroxy-7, 8-dihydroisomorphine

Table 6

| Compound | $AtD_{50}$mg/kg oral | Ratio codeine/drug |
|---|---|---|
| Codeine | 100.0 (66.67–150) | 1.00 |
| Morphine | 74.0 (51.03–107.30) | 1.35 |
| 14-OH-azidomorphine* | 10.0 (7.40–13.50) | 10.00 |

*6-deoxy-6-azido-14-hydroxy-7, 8-dihydroisomorphine

Note
$AtD_{50}$ means anti-tussive dose, s.c. (subcutaneous)

Tables 7 and 8 show the inhibitory activity of 14-hydroxy-azidomorphine and reference anti-tussives on electrical stimulation induced coughing in cats.

Table 7

| Compound | $AtD_{50}$mg/kg i.v. | Ratio Codeine/drug |
|---|---|---|
| Codeine | 1.45 | 1.00 |
| Azidocodeine | 0.40 | 3.63 |
| 14-OH-azidocodeine | 0.60 | 2.42 |
| Morphine | 0.61 | 2.38 |
| 14-OH-azidomorphine* | 0.012 | 120.83 |

*6-deoxy-6-azido-14-hydroxy-7, 8-dihydroisomorphine

Table 8

| Compound | AtD$_{100}$mg/kg i.v. | Ratio codeine/drug |
|---|---|---|
| Codeine | 5.07 ± 1.87 | 1.00 |
| Azidocodeine | 1.08 ± 0.04 | 4.69 |
| 14-OH-azidocodeine | 1.47 ± 0.07 | 2.91 |
| Morphine | 1.28 ± 0.32 | 3.96 |
| 14-OH-azidomorphine* | 0.02 ± 0.002 | 253.50 |

*6-deoxy-6-azido-14-hydroxy-7, 8-dihydroisomorphine

RESULTS

The data in Tables 5 through 8 clearly show that 14-hydroxy-azidomorphine* is a superior anti-tussive to those anti-tussives currently in use and which have similar formulae to the 14-hydroxy-azidomorphine*. It should be particularly pointed out that when 14-hydroxy-azidomorphine* was injected subcutaneously into rats, the compound was found to be 904 times more potent as an anti-tussive than codeine.
* 6-deoxy-6-azido-14-hydroxy-7, 8-dihydroisomorphine

METHODS

Blood pressure changes were studied in cats anesthetized with pentabarbitone sodium (35 mg/kg, i.p.). The substances were injected into the right femoral vein, responses to drugs were measured by means of a mercury manometer and recorded on a smoke cylinder. Since the hypotensive effects of morphine decrease on repeated administration, the blood pressure changes were from the responses to the very first injections of the substances.

RESULTS

The substances studied, except azidocodeine and 14-hydroxy-azidocodeine, lowered blood pressure, Vasodepressor responses ranged between 26 and 45 mm Hg. The hypotension produced by the drugs reached its maximal value within 1 to 2 minutes. In most experiments, blood pressure tended to increase 10 to 20 minutes after drug injection, but rarely returned to the initial value. In a few animals, blood pressure remained at a depressed or slightly elevated level throughout the experiment. On successive administrations of the drugs, tolerance to the vasodepressor responses developed rapidly and cross tolerance between morphine, codeine, azidomorphine and 14-hydroxyazidomorphine* was observed.
*6-deoxy-6-azido-14-hydroxy-7, 8-dihydroisomorphine Of the drugs under test only morphine produced a biphasic hypotensive effect. Blood pressure fell rapidly after morphine administration, then increased somewhat within one minute and remained unchanged for a longer period. No tolerance developed to the rapid phase of vasodepressor responses to morphine: it could be elicited by many successive injections of the drug.

Table V shows that the 14-hydroxy-azidomorphine* produced the greatest drop in blood pressure of all compounds tested, namely a drop of 45 mm Hg.

We claim:

1. 6-Deoxy-6-azido-14-hydroxy-7, 8-dihydroisomorphine or a pharmaceutically acceptable salt thereof.

* * * * *

TABLE 9

Vasodepressov responses to morphine, azidomorphine, 14-OH-azidomorphine*, azidocodeine and 14-OH-azidocodeine in anesthetized cats

| Compounds | Y.V. Dose mg/kg | Blood pressure mm Hg means ± S.E. | | Change in blood pressure mm Hg | No. of Expts. |
|---|---|---|---|---|---|
| | | Control | After Drug | | |
| Morphine | 1.03 | 130 ± 1.3 | 92 ± 1.0 | 39 ± 2.1 | 4 |
| Azidomorphine | 0.0035 | 143 ± 1.9 | 103 ± 9.3 | 40 ± 3.4 | 4 |
| 14-OH-azidomorphine* | 0.035 | 142 ± 3.8 | 97 ± 4.5 | 45 ± 5.8 | 5 |
| Codeine | 1.5 | 128 ± 6.1 | 98 ± 5.3 | 26 ± 4.9 | 4 |
| Azidocodeine | 0.5 | 128 ± 7.5 | 122 ± 5.2 | 6 ± 3.8 | 4 |
| 14-OH-azidocodeine | 0.5 | 129 ± 7.5 | 126 ± 6.6 | 3 ± 1.3 | 4 |

*6-deoxy-6-azido-14-hydroxy-7, 8-hydroisomorphine